US012582651B2

(12) United States Patent
Lee et al.

(10) Patent No.: US 12,582,651 B2
(45) Date of Patent: Mar. 24, 2026

(54) PHARMACEUTICAL COMPOSITION COMPRISING TADALAFIL OR PHARMACEUTICALLY ACCEPTABLE SALT THEREOF AND DUTASTERIDE OR PHARMACEUTICALLY ACCEPTABLE SALT THEREOF EXHIBITING NOVEL DISSOLUTION RATE

(71) Applicant: DONG KOOK PHARM. CO., LTD., Seoul (KR)

(72) Inventors: Ye Ri Lee, Gyeonggi-do (KR); Sung Hoon Jun, Gyeonggi-do (KR); Jong Sil Kim, Gyeonggi-do (KR); Kye Wan Lee, Seoul (KR)

(73) Assignee: DONG KOOK PHARM. CO., LTD., Seoul (KR)

( * ) Notice: Subject to any disclaimer, the term of this patent is extended or adjusted under 35 U.S.C. 154(b) by 308 days.

(21) Appl. No.: 18/269,379

(22) PCT Filed: Dec. 30, 2021

(86) PCT No.: PCT/KR2021/020236

§ 371 (c)(1),
(2) Date: Jun. 23, 2023

(87) PCT Pub. No.: WO2022/146061

PCT Pub. Date: Jul. 7, 2022

(65) Prior Publication Data

US 2024/0075028 A1 Mar. 7, 2024

(30) Foreign Application Priority Data

Dec. 31, 2020 (KR) ........................ 10-2020-0188774

(51) Int. Cl.

| | |
|---|---|
| ***A61K 31/4985*** | (2006.01) |
| ***A61K 9/16*** | (2006.01) |
| ***A61K 9/20*** | (2006.01) |
| ***A61K 31/58*** | (2006.01) |
| ***A61P 13/08*** | (2006.01) |
| ***A61P 15/10*** | (2006.01) |

(52) U.S. Cl.

CPC ........ *A61K 31/4985* (2013.01); *A61K 9/1611* (2013.01); *A61K 9/1617* (2013.01); *A61K 9/1641* (2013.01); *A61K 9/1652* (2013.01); *A61K 9/2009* (2013.01); *A61K 9/2013* (2013.01); *A61K 9/2018* (2013.01); *A61K 9/2031* (2013.01); *A61K 9/2054* (2013.01); *A61K 9/2077* (2013.01); *A61K 31/58* (2013.01); *A61P 13/08* (2018.01); *A61P 15/10* (2018.01); *A61K 2300/00* (2013.01)

(58) Field of Classification Search

None

See application file for complete search history.

(56) References Cited

U.S. PATENT DOCUMENTS

| | | | | |
|---|---|---|---|---|
| 2015/0313908 A1* | 11/2015 | Mjalli | ..................... | A61P 43/00 544/101 |
| 2019/0216827 A1* | 7/2019 | Baik | .................... | A61K 9/4858 |

FOREIGN PATENT DOCUMENTS

| | | |
|---|---|---|
| KR | 10-2009-0021380 A | 3/2009 |
| KR | 10-2016-0023962 A | 3/2016 |
| KR | 10-1716878 B1 | 3/2017 |
| KR | 10-1745425 B1 | 6/2017 |
| KR | 10-1780739 B1 | 9/2017 |
| KR | 10-1835506 B1 | 3/2018 |
| KR | 10-2018-0036638 A | 4/2018 |

OTHER PUBLICATIONS

English translation for KR 101835506 B1. (Year: 2018).*
International Search Report from corresponding PCT Application No. PCT/KR2021/020236, dated Apr. 11, 2022.
Mete Ozkidik, et al. "Efficacy of tadalafil treatment on erectile dysfunction in patients under dutasteride treatment: A prospective non-randomized comparative study", Turk J Urol. Jul. 2018; 44(4): 294-297.
Remington's The Science and Practice of Pharmacy, 21st Ed., Lippincott Williams & Wilkins (2005).
Handbook of Pharmaceutical Excipients (Rowe, Ed., APhA Publications, 2017).

* cited by examiner

*Primary Examiner* — Sin J Lee
(74) *Attorney, Agent, or Firm* — Harness, Dickey & Pierce, P.L.C.

(57) ABSTRACT

Provided is a pharmaceutical composition comprising as active ingredients: 5 mg of tadalafil or a pharmaceutically acceptable salt thereof; and 0.5 mg of dutasteride or a pharmaceutically acceptable salt thereof, wherein the dissolution rate of tadalafil under the dissolution conditions of a paddle rate of 50 rpm in 500 mL of a dissolution solution having a pH of 1.2 and containing 0.25% of SLS is 60-75% after 5 minutes and 80% or more after 30 minutes, and the dissolution rate of dutasteride under the dissolution conditions of a paddle rate of 50 rpm in 500 mL of a dissolution solution containing water and 0.1% of SLS is 50% or more after 15 minutes and 85% or more after 30 minutes.

3 Claims, 7 Drawing Sheets

PHARMACEUTICAL COMPOSITION COMPRISING TADALAFIL OR PHARMACEUTICALLY ACCEPTABLE SALT THEREOF AND DUTASTERIDE OR PHARMACEUTICALLY ACCEPTABLE SALT THEREOF EXHIBITING NOVEL DISSOLUTION RATE

CROSS-REFERENCE TO RELATED APPLICATION

This application is a national phase application of PCT Application No. PCT/KR2021/020236, filed on 30 Dec. 2021, which claims priority to and benefit of Korean Patent Application No. 10-2020-0188774, filed on 31 Dec. 2020. The entire disclosure of the application identified in this paragraph is incorporated herein by reference.

TECHNICAL FIELD

The present invention relates to a pharmaceutical composition exhibiting a novel dissolution rate. More specifically, the present invention relates to a pharmaceutical composition comprising tadalafil or a pharmaceutically acceptable salt thereof (hereinafter abbreviated as 'tadalafil') and dutasteride or a pharmaceutically acceptable salt thereof (hereinafter abbreviated as 'dutasteride') as active ingredients. The present invention also provides, in a pharmaceutical composition comprising tadalafil and dutasteride as active ingredients, a method for easily predicting in vivo absorption through an in vitro dissolution test. Furthermore, the present invention relates to a pharmaceutical composition comprising tadalafil-containing granules and dutasteride-containing granules having a specific particle size distribution to exhibit such a dissolution rate.

BACKGROUND ART

Korean Patent No. 1745425 discloses a composite emulsion composition for oral administration, comprising dutasteride and tadalafil. The emulsion composition disclosed in this document comprises the two drugs, dutasteride and tadalafil, in one unit formulation, but it has no problem of stability degradation, is conveniently manufactured, reduces pill burden, and exhibits equivalent drug dissolution and the same medicinal effect as each of the single formulations, allowing for simultaneous treatment of erectile dysfunction and prostatic hyperplasia and thus increasing patient's drug compliance.

Korean Patent No. 1712524 relates to, as a composite formulation composition comprising a tadalafil formulation and a dutasteride formulation, a composite formulation composition comprising tadalafil and dutasteride and a method for preparing the same. This document discloses a composite formulation composition prepared by mixing a dutasteride formulation and a tadalafil formulation; and a method for preparing the same, wherein the dutasteride formulation comprises a mixed solution comprising dutasteride, diethylene glycol monoethyl ether, mono/di-glyceride and, polyoxyl castor oil; and an adsorbent, the mixed solution being adsorbed on an adsorbent, and wherein the tadalafil formulation is prepared as granules by preparing a suspension comprising tadalafil, a surfactant, a water-soluble polymer, and solvent.

Korean Patent No. 1780739 discloses a composite formulation comprising a phosphodiesterase-5 inhibitor, for example, tadalafil, as a first active ingredient, and a 5-α-reductase inhibitor, for example, dutasteride, as a second active ingredient. This document discloses as a technical feature that a 5-α-reductase inhibitor is included in a coating layer, and the effect is to provide a synergic effect in the treatment and alleviation of prostatic hyperplasia by including two types of drugs for the treatment of prostatic hyperplasia with different pharmacological mechanisms in one formulation, thereby increasing the patient's drug compliance.

However, none of the documents described above specifically mentions or discloses a feature for a correlation between an in vitro dissolution test and in vivo absorption behavior in a pharmaceutical composition comprising tadalafil and dutasteride as active ingredients.

PRIOR ARTS

Patent Documents

Korean Patent No. 1745425
Korean Patent No. 1712524
Korean Patent No. 1780739

Non-Patent Documents

Efficacy of tadalafil treatment on erectile dysfunction in patients under dutasteride treatment: A prospective non-randomized comparative study (Turk J Urol. 2018 Jul.; 44(4): 294-297.)

DETAILED DESCRIPTION OF THE INVENTION

Technical Problem

The technical problem to solve is to investigate a correlation between an in vitro dissolution pattern and in vivo absorption behavior of a pharmaceutical composition (composite formulation) comprising tadalafil and dutasteride as active ingredients in order to derive dissolution conditions and dissolution rate that can make the in vivo absorption pattern of each active ingredient from a single formulation comprising tadalafil as an active ingredient and a single formulation comprising dutasteride as an active ingredient equal to the in vivo absorption pattern of each active ingredient from the combination composition. In this way, the present invention provides a pharmaceutical composition comprising, as active ingredients, tadalafil and dutasteride which have a firm in vitro in vivo correlation (hereinafter referred to as 'IVIVC') between in vitro dissolution test results and in vivo absorption pattern under specific dissolution conditions.

Technical Solution

The technical solution described above is solved by providing a pharmaceutical composition comprising 5 mg of tadalafil or a pharmaceutically acceptable salt thereof and 0.5 mg of dutasteride or a pharmaceutically acceptable salt thereof as active ingredients, wherein a dissolution rate of tadalafil under dissolution conditions of a 50 rpm paddle rate in 500 mL of an eluate comprising 0.25% SLS at pH 1.2 is 60 to 75% in 5 minutes and more than 80% in 30 minutes, and a dissolution rate of dutasteride under dissolution conditions of a 50 rpm paddle rate in 500 mL of an eluate comprising water and 0.1% SLS is 50% or more at 15 minutes and 85% or more at 30 minutes. As a specific means of exhibiting the dissolution rates above, the particle size of tadalafil-containing granules may be adjusted so that D10 may be 30 μm or less, D50 may be 70 to 130 μm, and D90 may be 250 to 350 μm, and the particle size of dutasteride-containing granules may be adjusted so that D10 may be 15 μm or less, D50 may be 25 to 40 μm, and D90 may be 90 to 150 μm.

Advantageous Effects

In preparing a pharmaceutical composition comprising tadalafil and dutasteride as active ingredients, a drug formulation development period may be shortened by deriving dissolution conditions and dissolution rates that can accurately predict an in vitro absorption pattern. Furthermore, a therapeutic effect is maximized by improving a dissolution rate of each single ingredient.

BEST MODE

Figure 1:
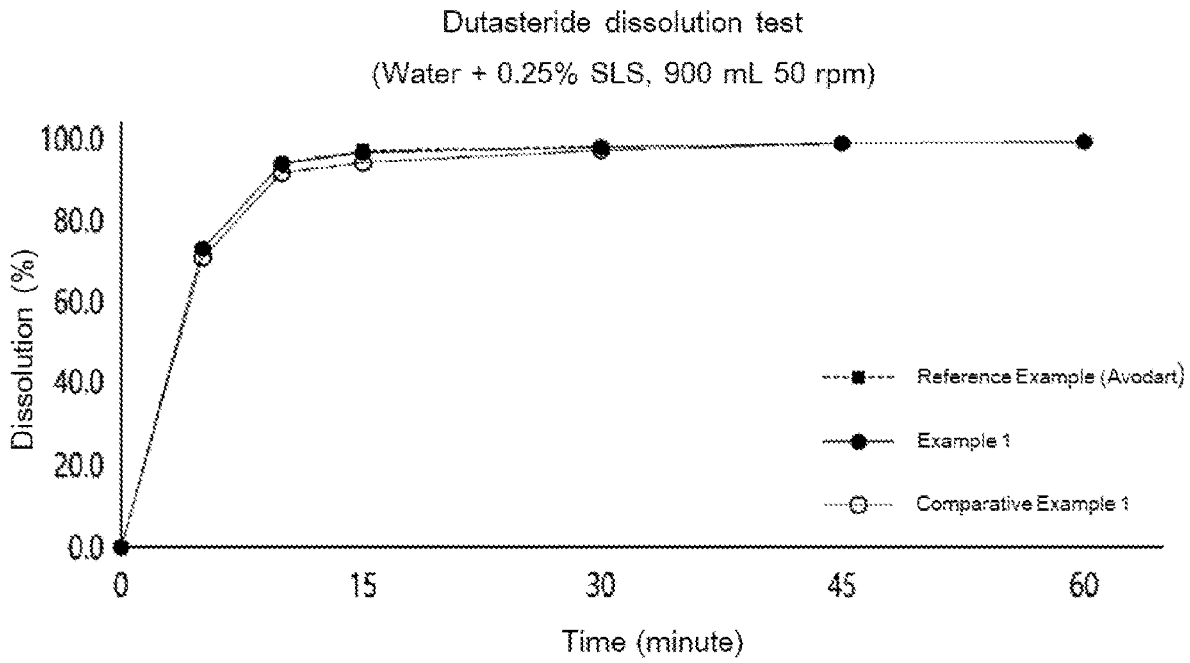
FIG. 1 is a graph showing the results when a dissolution test is performed according to the conventional specification and test method for Example 1, Comparative Example 1, and Reference Example (Avodart).

A drug development process involves in vitro testing, animal testing, and in vivo testing with human subjects. This applies to not only the process of new drug development but also the development of so-called drugs requiring data submission or generic drugs, which are called Incrementally Modified Drugs.

Efforts to reduce in vivo testing conducted with human subjects are being actively attempted based on scientific evidence. As a part of this, efforts to replace in vivo tests with in vitro tests are being actively made worldwide. However, the dissolution and absorption process of a drug from a medicine administered in vivo occurs in a complicated system involving various physiological substances and the in vivo factors to drug absorption are also very diverse. Therefore, there is a limit in evaluating the in vivo pharmacokinetics of a drug only with in vitro test methods. Therefore, it is necessary to study the in vitro test conditions that can most appropriately reflect the in vivo state through an in vivo and in vitro correlation study. The IVIVC correlation development and predictivity evaluation results may establish a dissolution test method as a surrogate index for human bioequivalence tests, and based on this, the number of bioequivalence tests to be performed during the processes of expanding a manufacturing scale, making changes after approval, and acquiring the initial approval may be reduced.

In vitro dissolution testing is important in process control and quality assurance, confirmation of stable release characteristics of products over time, and making certain regulatory decisions in minor changes of a formulation or changes in the manufacturer. With regard to a controlled-release formulation for oral administration, the dissolution test can also be used as an indicator to control the quality of the manufacturing process and to represent the in vivo pharmacokinetics of the formulation.

The present invention relates to a pharmaceutical composition comprising tadalafil and dutasteride as active ingredients. Tadalafil is an active ingredient of a drug marketed under the trade name Cialis® and has the structure of Chemical Formula 1 below.

[Chemical Formula 1]

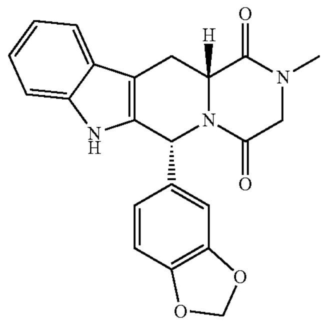

Tadalafil is a selective and reversible inhibitor of cyclic guanosine monophosphate (cGMP)-specific phosphodiesterase type 5 (hereinafter referred to as PDE-5). Tadalafil is known that it can be used for the treatment of erectile dysfunction and benign prostatic hyperplasia or for the treatment of patients with both erectile dysfunction and benign prostatic hyperplasia.

Dutasteride is an active ingredient of a drug marketed under the trade name Avodart® and has the structure of Chemical Formula 2 below.

[Chemical Formula 2]

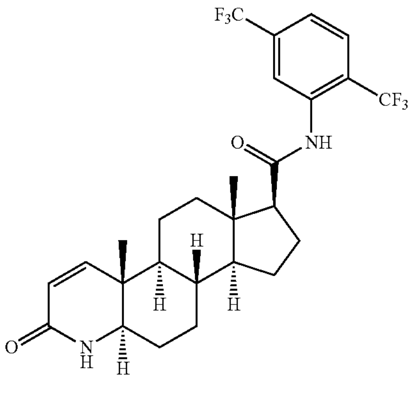

Dutasteride is a dual 5-alpha reductase inhibitor inhibiting both type 1 and type 2 of 5-alpha reductase. Dutasteride is known to be useful in the treatment of benign prostatic hyperplasia, prostate cancer, and male pattern alopecia, as it inhibits the conversion of testosterone to dihydrotestosterone (DHT).

Prostatic hyperplasia is a very common disease in which the size of the prostate increases with age, causing abnormalities in various urination functions. For the treatment of prostatic hyperplasia, administration of a 5-alpha reductase inhibitor, a drug that reduces the size of the prostate, is effective, but there are cases where the improvement effect does not appear immediately. Accordingly, combined administration may be performed with other drugs for improving the symptoms, and the other drugs comprise tadalafil. Therefore, by providing a composite formulation comprising dutasteride and tadalafil as active ingredients, the effects of reducing the size of the prostate and improving the symptoms may be expected at the same time.

In preparing a composite formulation prepared as a single formulation of active ingredients of two types of single formulations that have already known and marketed with approval from the drug approval authority, it is necessary to ensure that the in vivo absorption pattern of the active ingredients contained in the subject composite formulation is equivalent to the in vivo absorption pattern of the active ingredients of the single formulations that have already approved. In addition, the equivalency must be verified by a clinical test performed with human subjects. However, it is often the case that the drug dissolution and absorption pattern of the same active ingredients from single formulations is not the same as their drug dissolution and absorption pattern from a composite formulation. Therefore, even when the dissolution rate of the active ingredients from single formulations is adjusted to be equivalent to their dissolution rate from a composite formulation simply by performing a dissolution test, the absorption pattern in human body found in actual clinical trials is often different. Accordingly, it is necessary to repeat the formulation design while undergoing several clinical trials. Therefore, the consumption of relevant cost and time is of the biggest obstacles encountered in the process of developing of a composite drug.

According to the US FDA guidance published in September 1997, the purpose of studying the IVIVC is to enable the dissolution, solubility, and intestinal permeability tests to be used as alternative methods to bioavailability tests. Therefore, once the IVIVC is established, the bioequivalence between two formulations can be secured through a dissolution test when expanding the production or changing the additives after drug approval. Meanwhile, although dissolution tests are widely used by the testing institutes in Korea for quality control of orally administered solid formulations, the in vitro dissolution test data alone often fail to accurately predict the in vivo pharmacokinetics. Predicting the in vitro absorption pattern based on the in vitro dissolution test results is far more difficult in the case of composite formulations.

In this situation, the present inventors have reached the present invention by obtaining the knowledge that, in a pharmaceutical composition comprising tadalafil and dutasteride, the dissolution rate under specific dissolution conditions has a firm correlation with the in vitro absorption pattern.

Specifically, the present inventors obtained the novel knowledge that in a pharmaceutical composition comprising tadalafil and dutasteride as active ingredients, when the dissolution rate of tadalafil under dissolution conditions of a 50 rpm paddle rate in 500 mL of an eluate comprising 0.25% SLS at pH 1.2 is 60 to 75% in 5 minutes and more than 80% in 30 minutes and the dissolution rate of dutasteride under dissolution conditions of a 50 rpm paddle rate in 500 mL of an eluate comprising water and 0.1% SLS is 50% or more at 15 minutes and 85% or more at 30 minutes, the in vitro absorption pattern of the pharmaceutical composition becomes equivalent to that of a single formulation comprising tadalafil as an active ingredient and a single formulation containing dutasteride as an active ingredient.

In other words, when the dissolution conditions are out of those described above, the in vivo absorption pattern of the pharmaceutical composition comprising tadalafil and dutasteride is not the same as that of each active ingredient of single formulations each comprising tadalafil and dutasteride. Therefore, the pharmaceutical composition satisfying the specific dissolution conditions described in the present invention has the advantage that drug development can be performed by investing minimal cost and time without repeated clinical trials.

As one technical means to exhibit the dissolution conditions described above, the particle size distribution of granules comprising tadalafil and dutasteride may be controlled. The pharmaceutical composition of the present invention comprises granules comprising tadalafil (hereinafter referred to as 'tadalafil granules') and granules comprising dutasteride (hereinafter referred to as 'dutasteride granules'). Specifically, the tadalafil formulation is granulated by preparing a suspension comprising tadalafil, a surfactant, a water-soluble polymer, and a solvent, and dutasteride granules are granulated by dissolving in a solution such as mono/di-glyceride and/or diethylene glycol monoethyl ether and adsorbing on an adsorbent.

The present inventors have obtained the knowledge that the particle size distribution of the tadalafil granules and dutasteride granules affects the micro-dissolution pattern of the pharmaceutical composition according to the present invention. Specifically, the dissolution conditions described in the present invention were obtained by finely controlling the dissolution pattern of releasing for a relatively short time of 30 minutes, and such dissolution pattern may be achieved by more precisely controlling the particle size distribution of granules comprising each active ingredient. Specifically, when the particle size of tadalafil-containing granules is adjusted so that D10 may be 30 μm or less, D50 may be 70 to 130 μm, and D90 may be 250 to 350 μm, and the particle size of dutasteride-containing granules is adjusted so that D10 may be 15 μm or less, D50 may be 25 to 40 μm, and D90 may be 90 to 150 μm, the dissolution pattern of the present invention may be expressed. D10 refers to the particle diameter corresponding to the lower 10% of the cumulative volume in a cumulative particle size distribution according to the particle size distribution system, and D50 and D90 refers to the particle diameters corresponding to 50% and 90%, respectively. The particle size distribution is controlled and measured by the pulverizing methods and measurement methods that are widely known in the technical field. For example, commonly known methods for controlling particle size distribution include pulverization using a microfluidizer, a zet-mill, a co-mill, a ball-mill, and the like, and granulation by a wet or dry granulation method. To confirm the control of particle size distribution, measurement may be performed by a dry measurement method using a laser diffraction particle size analyzer (e.g., HELOS (H0184) & RODOS, R5: 0.5/4.5 . . . 875 μm).

The pharmaceutical composition according to the present invention comprises: preparing tadalafil granules by preparing a suspension comprising tadalafil, a surfactant, a water-soluble polymer, and a solvent; dissolving dutasteride in a mono/di-glyceride and diethylene glycol monoethyl ether mixed solution and adsorbing on an adsorbent to prepare a dutasteride adsorbate and granulate the same to prepare dutasteride granules; and mixing the tadalafil granules and dutasteride granules, then filling or tableting by mixing pharmaceutically acceptable excipients, disintegrants, and additives.

Surfactants, water-soluble polymers, adsorbents, and pharmaceutically acceptable excipients, disintegrants, diluents, and additives included in the pharmaceutical composition of the present invention are not limited as long as they satisfy the dissolution conditions stipulated in the present invention, or satisfy the dissolution conditions while satisfying the particle size conditions of the granules stipulated in the present application, and the pharmaceutical composition is prepared by adopting a common formulation technology in manufacturing pharmacy. For example, the pharmaceutical composition may be prepared as various pharmaceutical composition by using the standard formulation techniques disclosed in Remington's The Science and Practice of Pharmacy, 21st Ed., Lippincott Williams & Wilkins (2005), etc., preferably as a table or capsule. Regarding surfactants, water-soluble polymers, adsorbents, and pharmaceutically acceptable excipients, disintegrants, diluents, and additives included in the pharmaceutical composition of the present invention, the document [Handbook of Pharmaceutical Excipients (Rowe, Ed., APhA Publications, 2017)], and the like may be referred to, and an excipient may be intragranular (i.e., incorporated within the granule) or extragranular (i.e., outside the granule).

As a surfactant included in the pharmaceutical composition of the present invention, a pharmaceutically acceptable surfactant may be used without any particular limitation, and preferably one selected from polyoxyethylene stearates, palmitic acid esters, sodium lauryl sulfate, poloxamer, and combinations thereof may be used, and more preferably, sodium lauryl sulfate may be used, but is not limited thereto. A water-soluble polymer included in the pharmaceutical composition of the present invention may be selected from hydroxypropylcellulose, hydroxypropylmethylcellulose, polyvinylpyrrolidone, and combinations thereof. A solvent referred to in the present invention may be selected from methanol, ethanol, isopropyl alcohol, purified water, and combinations thereof.

As used in the present specification, the term "mono/diglyceride" comprehensively refers to monoglycerides, diglycerides, and mixtures thereof. In the present invention, as an adsorbent, a pharmaceutically acceptable adsorbent may be used without any particular limitation, and preferably, one selected from silicon dioxide, colloidal silicon dioxide, magnesium aluminate silicate, calcium silicate, magnesium aluminometasilicate, and combinations thereof may be used, and more preferably, magnesium silicate aluminate may be used.

In addition to the components described above, the pharmaceutical composition according to the present invention may further comprise common pharmaceutically acceptable additional ingredients, such as excipients, disintegrants, additives, and the like. Pharmaceutically acceptable excipients, disintegrants, additives, and the like may include, but are not limited to, calcium diphosphate, calcium sulfate, sugars such as lactose, glucose, and sucrose; starches, such as corn starch and potato starch; cellulose and derivatives thereof, such as sodium carboxymethyl cellulose, ethyl cellulose, and methyl cellulose; kaolin, powdered tragacanth; malt; gelatin; talc; solid lubricants such as stearic acid, magnesium stearate, and calcium stearate; calcium sulfate; mineral oil; vegetable oils such as hydrogenated vegetable oil, peanut oil, cottonseed oil, sesame oil, olive oil, corn oil and cacao oil; polyols such as propylene glycol, glycerin, sorbitol, inositol, mannitol and polyethylene glycol; alginic acid; emulsifiers such as polysorbates; wetting agents such as sodium lauryl sulfate, poloxamers; coloring agents; flavoring agents; tableting agents, stabilizing agents; antioxidants; preservatives, and the like.

Hereinafter, specific embodiments of the present invention will be described with reference to Examples. These Examples are merely illustrative to help the understanding of the present invention, and the scope of the present invention is not limited thereby.

Preparation of Examples 1-3

A pharmaceutical composition was prepared according to the composition shown in Table 1 below. For tadalafil granules, hydroxypropyl cellulose, sodium lauryl sulfate, and poloxamer were added to purified water and completely dissolved, and then tadalafil was added to disperse the resulting solution to prepare a suspension. After mixing microcrystalline cellulose, lactose hydrate, D-mannitol as diluents, low-substituted hydroxypropyl cellulose, and sodium croscarmellose as a disintegrant, the resulting mixture was combined into the suspension described above so that no problem in the content uniformity of tadalafil occurs in a granulation process. The granulated material was dried at a temperature of 60° C. to prepare granules comprising tadalafil. Dutasteride granules were prepared by firstly dissolving dutasteride in a mixed solution of mono/di-glyceride and diethylene glycol monoethyl ether. An adsorbate containing dutasteride was prepared by adsorbing the mixed solution prepared above was adsorbed to colloidal silicon dioxide, which is adsorbents and sodium lauryl sulfate. After mixing the tadalafil granules and dutasteride granules prepared above, D-mannitol, sodium croscarmellose, and magnesium stearate were added for tableting.

TABLE 1

| Item | Composition | Example 1 | Example 2 | Example 3 |
|---|---|---|---|---|
| Tadalafil granules | Tadalafil | 5 | 5 | 5 |
| | Microcrystalline cellulose | 13 | 13 | 13 |
| | Lactose hydrate | 58.7 | 36.0 | 87.7 |
| | D-mannitol | 65 | 87.7 | 36 |
| | Sodium lauryl sulfate | 2.5 | 2.5 | 2.5 |
| | Low-substituted hydroxypropyl cellulose | 150 | 150 | 150 |
| | Hydroxypropyl cellulose | 1.5 | 1.5 | 1.5 |
| | Sodium croscarmellose | 30 | 30 | 30 |
| | Poloxamer | 3.3 | 3.3 | 3.3 |
| Dutasteride granules | Dutasteride | 0.5 | 0.5 | 0.5 |
| | Mono and diglycerides | 6 | 6 | 6 |
| | Diethylene glycol monoethyl ether | 14 | 14 | 14 |
| | Colloidal silicon dioxide | 20 | 20 | 20 |
| | Sodium lauryl sulfate | 20 | 20 | 20 |
| Post-mixing | D-mannitol | 284.5 | 284.5 | 284.5 |
| | Sodium croscarmellose | 20 | 20 | 20 |
| | Magnesium stearate | 6 | 6 | 6 |

(The numerical values described in the table above indicate the content per tablet in mg.)

The particle size of the tadalafil granules and dutasteride granules prepared in Examples 1 to 3 are shown in Table 2 below.

TABLE 2

| Item | Granules | D10 | D50 | D90 |
|---|---|---|---|---|
| Example 1 | Tadalafil granules | 27.33 | 102.56 | 300.17 |
| | Dutasteride granules | 8.64 | 35.47 | 116.73 |
| Example 2 | Tadalafil granules | 24.42 | 90.65 | 270.56 |
| | Dutasteride granules | 8.64 | 35.47 | 116.73 |
| Example 3 | Tadalafil granules | 28.25 | 125.24 | 330.41 |
| | Dutasteride granules | 8.64 | 35.47 | 116.73 |

Preparation of Comparative Examples 1-3

| Item | Composition | Comparative Example 1 | Comparative Example 2 | Comparative Example 3 |
|---|---|---|---|---|
| Tadalafil granules | Tadalafil | 5 | 5 | 5 |
| | Microcrystalline cellulose | 13 | 13 | 13 |
| | Lactose hydrate | 63 | 36.0 | 87.7 |
| | D-mannitol | — | 87.7 | 36 |
| | Sodium lauryl sulfate | 2.5 | 2.5 | 2.5 |
| | Low-substituted hydroxypropyl cellulose | — | 150 | 150 |
| | Hydroxypropyl cellulose | 3 | 1.5 | 1.5 |
| | Sodium croscarmellose | 6 | 30 | 30 |
| | Poloxamer | — | 3.3 | 3.3 |
| Dutasteride granules | Dutasteride | 0.5 | 0.5 | 0.5 |
| | Mono and diglycerides | 20 | 6 | 6 |
| | Diethylene glycol monoethyl ether | 20 | 14 | 14 |
| | Polyoxyl 35 castor oil | 40 | — | — |
| | Magnesium aluminometasilicate | 20 | — | — |
| | Colloidal silicon dioxide | — | 20 | 20 |
| | Sodium lauryl sulfate | 10 | 20 | 20 |
| Post-mixing | D-mannitol | 284.5 | 284.5 | 284.5 |
| | Sodium croscarmellose | 20 | 20 | 20 |
| | Magnesium stearate | 6 | 6 | 6 |

(The numerical values described in the table above indicate the content per tablet in mg.)

Comparative Examples 1 to 3 were prepared in the same manner as in Examples 1 to 3, except that the particle size distribution of tadalafil granules and dutasteride granules of Comparative Examples 1 to 3 was adjusted as described in Table 3.

TABLE 3

| Item | Granules | D10 | D50 | D90 |
|---|---|---|---|---|
| Comparative Example 1 | Tadalafil granules | 14.04 | 143.95 | 483.07 |
| | Dutasteride granules | 13.84 | 43.06 | 105.67 |
| Comparative Example 2 | Tadalafil granules | 6.85 | 72.51 | 503.89 |
| | Dutasteride granules | 8.64 | 35.47 | 116.73 |
| Comparative Example 3 | Tadalafil granules | 4.74 | 39.82 | 454.07 |
| | Dutasteride granules | 8.64 | 35.47 | 116.73 |

Experimental Example 1

Figure 2:
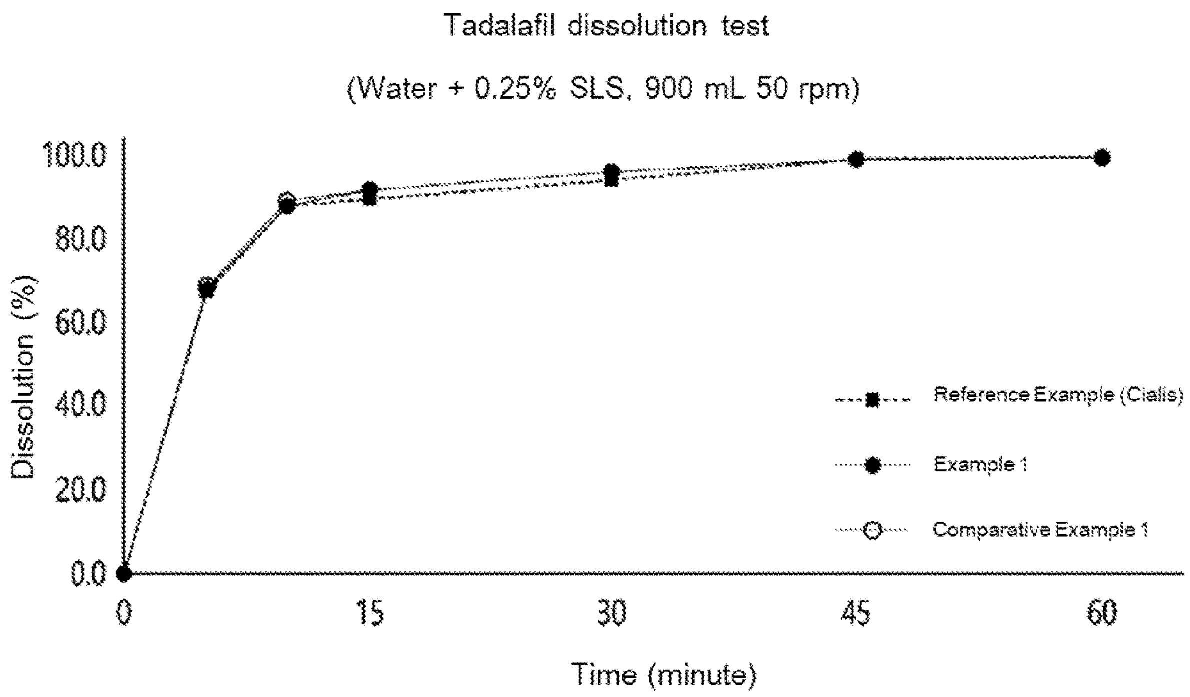
FIG. 2 is a graph showing the results when a dissolution test is performed according to the conventional specification and test method for Example 1, Comparative Example 1, and Reference Example (Cialis).

As Example 1, Comparative Example 1, and as a Reference Example, dissolution was performed by using Avodart tablet (dutasteride 0.5 mg) and Cialis tablet (tadalafil 5 mg) under the conditions described below, and the dissolution rate results of dutasteride are shown in FIG. 1 and Table 4 and the dissolution rate results of tadalafil are shown in FIG. 2 and Table 5.

Dissolution Conditions

Water, 0.25% SLS 900 mL, 50 rpm

TABLE 4

| Minute | Reference example (Avodart) | Example 1 | Comparative Example 1 |
|---|---|---|---|
| 5 | 72.9 | 73.6 | 71.2 |
| 10 | 94.2 | 94.7 | 92.0 |
| 15 | 97.6 | 96.8 | 94.6 |
| 30 | 98.1 | 98.6 | 97.8 |
| 45 | 99.2 | 99.5 | 99.2 |
| 60 | 100.0 | 100.1 | 99.4 |

TABLE 5

| Minute | Reference example (Cialis) | Example 1 | Comparative Example 1 |
|---|---|---|---|
| 5 | 67.2 | 68.2 | 70.0 |
| 10 | 88.2 | 88 | 90.0 |
| 15 | 89.9 | 91.9 | 92.1 |
| 30 | 94.1 | 95.8 | 96.2 |
| 45 | 99.2 | 98.5 | 99.0 |
| 60 | 100.0 | 99.5 | 99.4 |

As shown in Tables 4 and 5 and FIGS. 1 and 2 above, there was no difference in the dissolution rate between Reference Example, Example 1 and Comparative Example 1 under the dissolution conditions of the general specification and test method. Therefore, an ordinary researcher of drug formulation would predict that both Example 1 and Comparative Example 1 have bioequivalence with Reference Example.

Experimental Example 2

Figure 3:
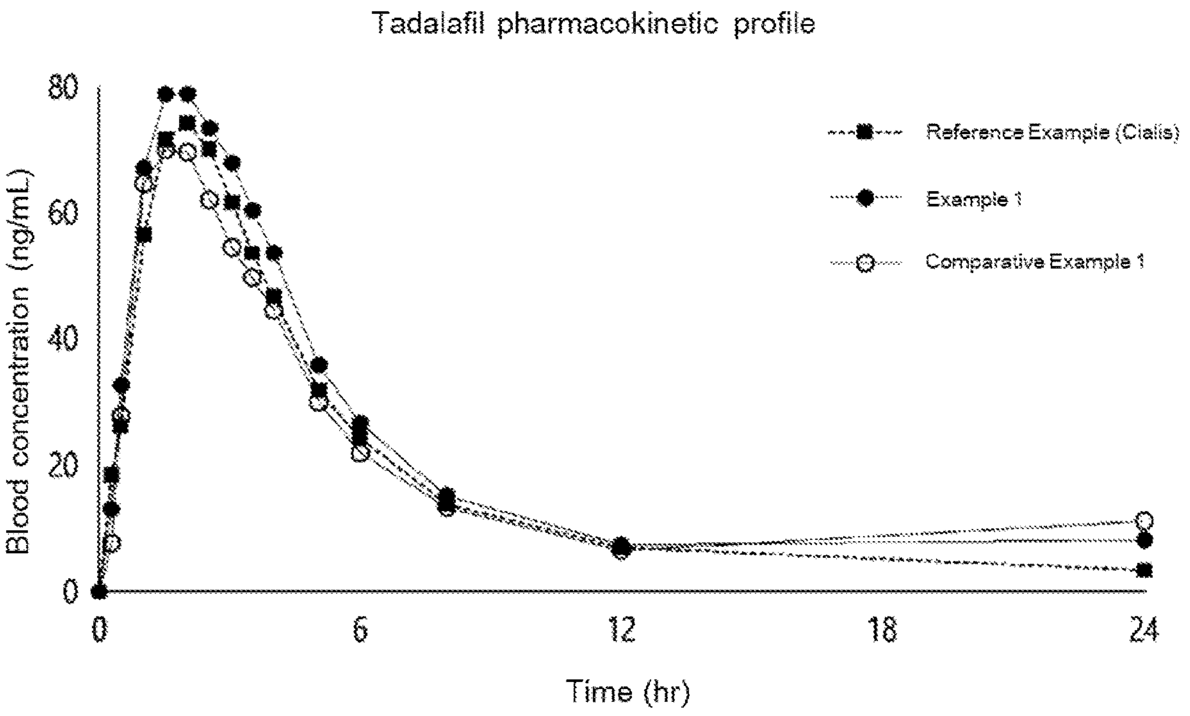
FIG. 3 is a graph showing the PK in beagle dogs for Example 1, Comparative Example 1 and Reference Example (Avodart).
Figure 4:
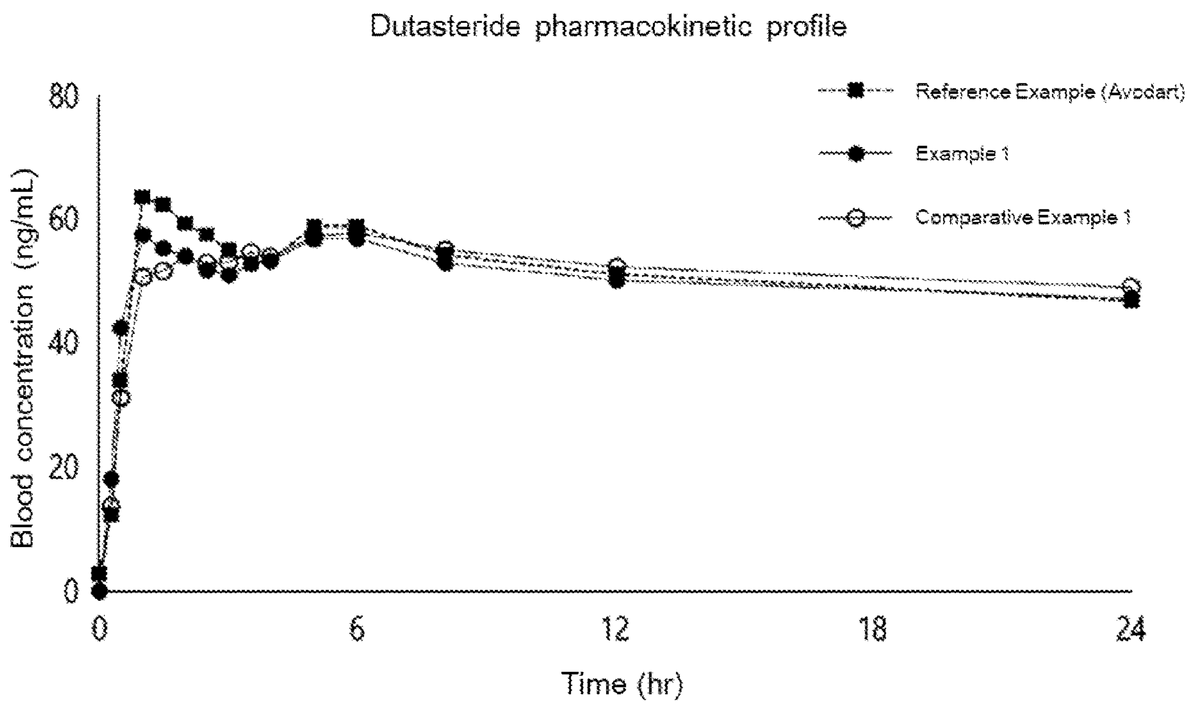
FIG. 4 is a graph showing the PK in beagle dogs for Example 1, Comparative Example 1 and Reference Example (Cialis).

The PK was measured with beagle dogs as subjects by using Reference Example, Example 1, and Comparative Example 1, and the trend of the blood drug concentration of tadalafil is shown in FIG. 3 and Table 6 and the trend of the blood drug concentration of dutasteride is shown in FIG. 4 and Table 7.

For pharmacokinetic evaluation, 15 beagle dogs (5 per group) were 3X3 cross-administered in each of the groups described below. The drug withdrawal period was set to be 2 weeks in consideration of the half-life of the drug. The blood sampling time was at intervals of 0, 0.25, 0.5, 1, 1.5, 2, 2.5, 3, 3.5, 4, 5, 6, 8, 12, 24, 48 in consideration of the peak blood concentrations of dutasteride and tadalafil.

[Test Drug Information]

Control group: Combined administration of 1 tablet of Cialis and 1 capsule of Avodart Test group 1: 1 tablet of Example 1

Test group 2: 1 tablet of Example 2

As shown in FIGS. 3 and 4 and Tables 6 and 7, Example 1 was biologically equivalent to Reference Example, but Comparative Example 1 was not equivalent to Reference Example. Considering the results of Experimental Example 1, where there was no difference in the dissolution rate between Reference Example, Example 1 and Comparative Example 1, the results described above indicate that, in a pharmaceutical composition comprising tadalafil and dutasteride as active ingredients, there is not a firm IVIVC between the in vitro dissolution pattern and the in vivo absorption pattern under the dissolution conditions of the general specification and test method

TABLE 6

| Test group | $C_{max}$ (ng/mL) | $C_{max}$ T/R ratio | $AUC_{all}$ (nghr/mL) | $AUC_{all}$ T/R ratio | $AUC_{INF}$ (nghr/mL) |
|---|---|---|---|---|---|
| Reference example (Cialis) | 80.92 ± 27.05 | — | 365.92 ± 214.72 | — | 382.91 ± 217.51 |
| Comparative Example 1 | 77.07 ± 33.23 | 0.91 | 353.88 ± 234.36 | 0.91 | 386.53 ± 264.74 |
| Example 1 | 92.67 ± 36.35 | 1.1 | 418.79 ± 207.41 | 1.17 | 458.69 ± 242.12 |

TABLE 7

| Test group | $C_{max}$ (ng/mL) | $C_{max}$ T/R ratio | $AUC_{all}$ (nghr/mL) | $AUC_{all}$ T/R ratio | $AUC_{INF}$ (nghr/mL) |
|---|---|---|---|---|---|
| Reference example (Avodart) | 70.83 ± 22.42 | — | 6067.84 ± 2278.85 | — | 6553.23 ± 2293.02 |
| Comparative Example 1 | 66.83 ± 22.32 | 0.94 | 6076.8 ± 2497.47 | 0.97 | 6449.5 ± 2479.33 |
| Example 2 | 67.94 ± 18.86 | 0.99 | 6335.33 ± 2447.36 | 1.04 | 6722.9 ± 2437.48 |

Experimental Example 3

A dissolution test was performed with Example 1, Comparative Example, 1 and Reference Examples (Avodart and Cialis tablets) under the dissolution conditions described below, and the dissolution rate for tadalafil is shown in Table 8 and FIG. 5 and the dissolution rate for dutasteride is shown in Table 9 and FIG. 6.

Tadalafil Dissolution Conditions pH 1.2, 0.25% SLS, 50 rpm, 500 mL

Dutasteride Dissolution Conditions

Water, 0.1% SLS, 50 rpm, 500 mL

TABLE 8

| Minute | Reference example (Cialis) | Example 1 | Comparative Example 1 |
|---|---|---|---|
| 5 | 65.9 | 72.9 | 63.4 |
| 15 | 83.8 | 85.3 | 69.0 |
| 30 | 84.1 | 86.5 | 70.1 |
| 45 | 85.6 | 86.4 | 70.7 |

TABLE 9

| Minute | Reference example (Avodart) | Example 1 | Comparative Example 1 |
|---|---|---|---|
| 5 | 49.2 | 55.7 | 31.5 |
| 15 | 66.9 | 87.6 | 36.5 |
| 30 | 77.7 | 88.3 | 36.7 |
| 45 | 86.0 | 90.2 | 43.8 |

Figure 5:
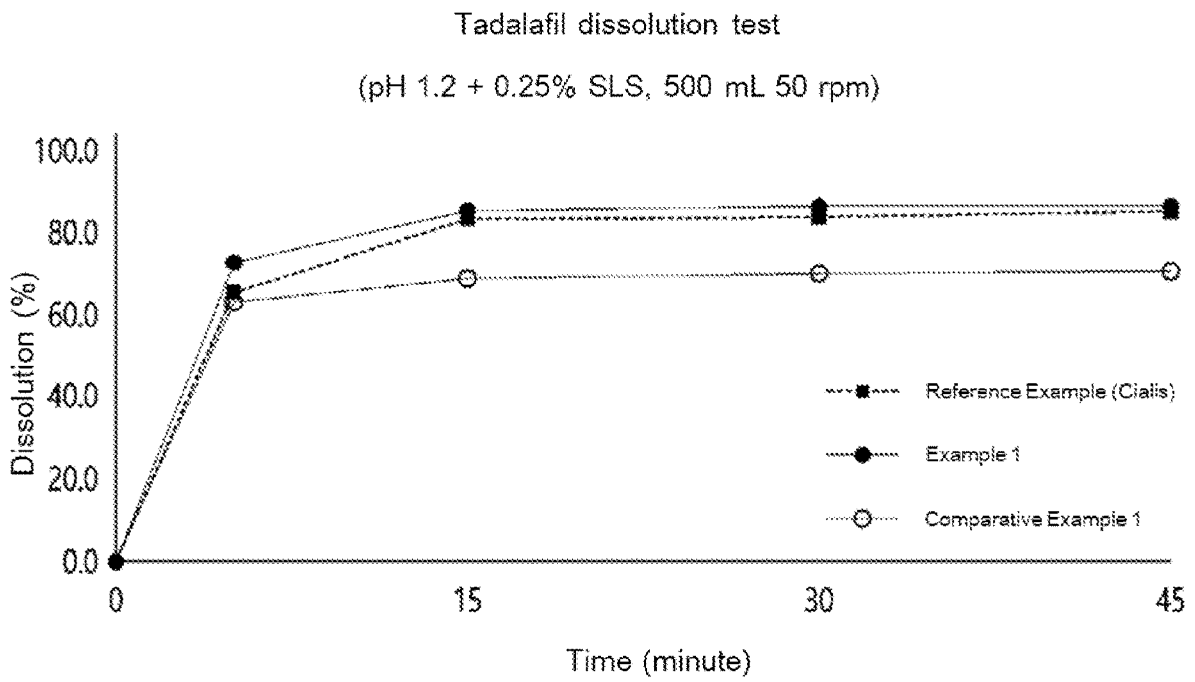
FIG. 5 is a graph showing the results of dissolution test of Example 1, Comparative Example 1, and Reference Example (Cialis) under the dissolution conditions of the present invention.
Figure 6:
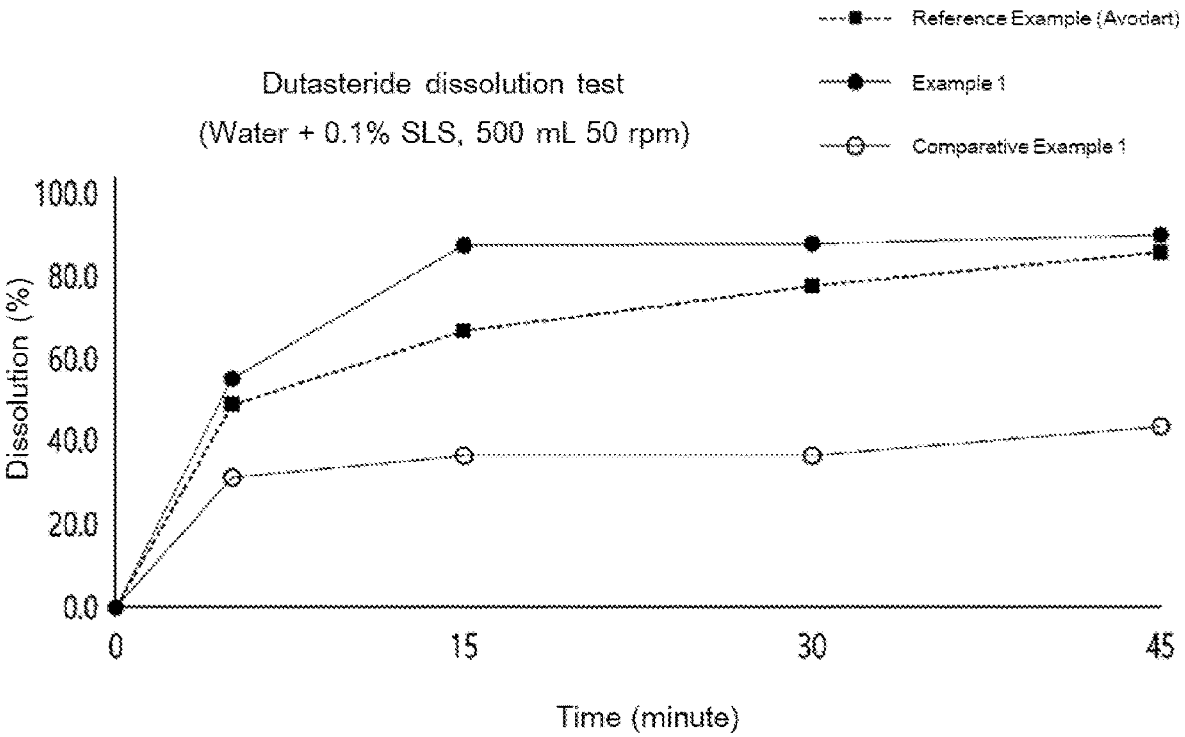
FIG. 6 is a graph showing the results of dissolution test of Example 1, Comparative Example 1, and Reference Example (Avodart) under the dissolution conditions of the present invention.

As shown in Tables 8 and 9 and FIGS. 5 and 6, Example 1 exhibited a dissolution rate of 60 to 75% in 5 minutes and more than 80% in 30 minutes under the tadalafil dissolution conditions of pH 1.2, 0.25% SLS, 50 rpm, 500 mL, and a dissolution rate of 50% or more in 15 minutes and 85% or more in 30 minutes under the dutasteride dissolution conditions of water, 0.1% SLS, 50 rpm, 500 mL.

Experimental Example 4

Figure 7:
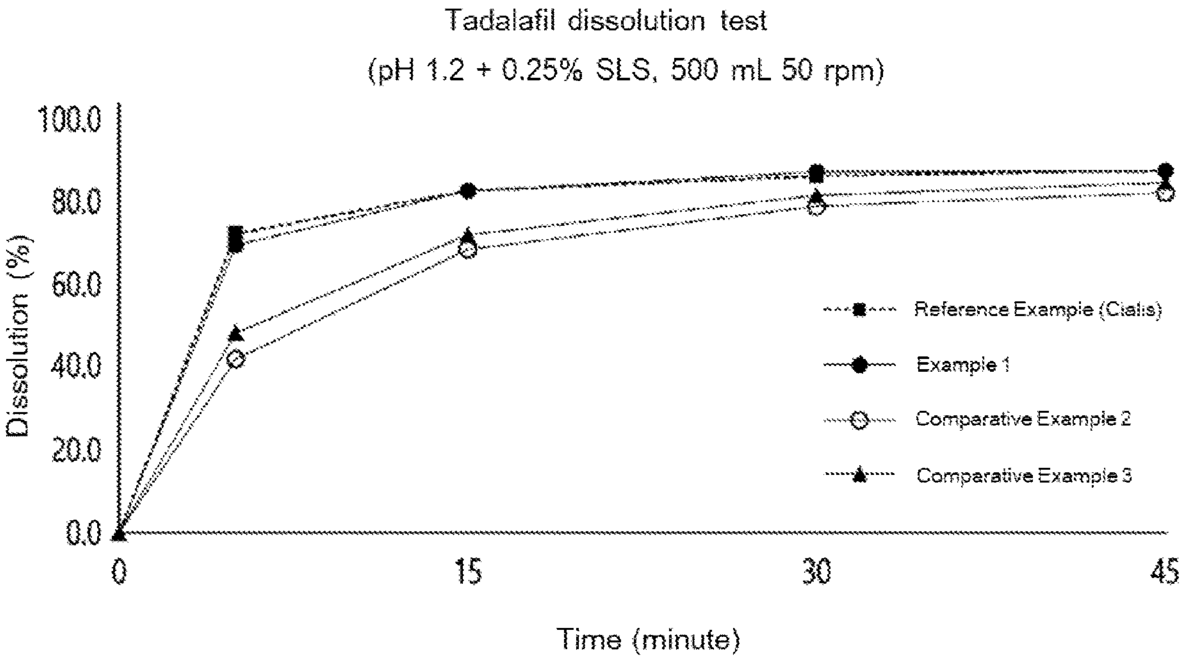
FIG. 7 is a graph showing the results of dissolution test of Example 1, Comparative Examples 2 and 3, and Reference Example (Cialis) under the dissolution conditions of the present invention.

The dissolution rate of tadalafil was measured for Example 1 and Comparative Examples 1, 2, and 3 under the dissolution test conditions according to the present invention, and the results are shown in Table 10 and FIG. 7.

TABLE 10

| Minute | Reference example (Cialis) | Example 1 | Comparative Example 2 | Comparative Example 3 |
|---|---|---|---|---|
| 5 | 72.9 | 70.0 | 42.4 | 48.8 |
| 15 | 83.0 | 83.3 | 69.0 | 72.6 |
| 30 | 86.9 | 87.9 | 79.5 | 82.1 |
| 45 | 88.0 | 88.0 | 82.7 | 85.0 |

From Table 10 and FIG. 7, it was confirmed that when the particle size distribution presented in the present invention is not satisfied, the dissolution condition of the present invention may not be satisfied.

INDUSTRIAL APPLICABILITY

When the dissolution conditions and dissolution rates described in the present invention are used in preparing a pharmaceutical composition comprising tadalafil and dutasteride as active ingredients, the in vivo absorption pattern of each active ingredient from the pharmaceutical composition and the in vivo absorption pattern of active ingredients from previous approved single formulations may be adjusted to be equivalent.

What is claimed is:

1. A pharmaceutical composition comprising:

granules comprising 5 mg of tadalafil or a pharmaceutically acceptable salt thereof; and granules comprising 0.5 mg of dutasteride or a pharmaceutically acceptable salt thereof as active ingredients, wherein a dissolution rate of tadalafil under dissolution conditions of a 50 rpm paddle rate in 500 mL of an eluate comprising 0.25% SLS at pH 1.2 is 60 to 75% in 5 minutes and more than 80% in 30 minutes, wherein a dissolution rate of dutasteride under dissolution conditions of a 50 rpm paddle rate in 500 mL of an eluate comprising water and 0.1% SLS is 50% or more at 15 minutes and 85% or more at 30 minutes, wherein the particle size of the granules comprising tadalafil or a pharmaceutically acceptable salt thereof is such that D10 is 30 μm or less, D50 is 70 to 130 μm, and D90 is 250 to 350 μm, wherein the particle size of the granules comprising dutasteride or a pharmaceutically acceptable salt thereof is such that D10 is 15 μm or less, D50 is 25 to 40 μm, and D90 is 90 to 150 μm, wherein the granules comprising tadalafil are granules prepared by preparing a suspension comprising tadalafil, a surfactant, a water-soluble polymer, and a solvent and granulating the same, and wherein the granules comprising dutasteride are granules prepared by dissolving dutasteride in a mixed oil solution comprising diethylene glycol monoethyl ether and mono/di-glyceride, adsorbing the resulting solution on an adsorbent, and granulating the same.

2. The pharmaceutical composition according to claim 1, wherein the dutasteride granules do not comprise polyoxyl castor oil.

3. The pharmaceutical composition according to claim 1, wherein the adsorbent is selected from silicon dioxide, colloidal silicon dioxide, magnesium aluminate silicate, calcium silicate, magnesium aluminometasilicate, or combinations thereof.

* * * * *